United States Patent [19]

Heifetz

[11] Patent Number: 4,775,681
[45] Date of Patent: Oct. 4, 1988

[54] METHOD OF TREATING FUNGAL INFECTIONS WITH TRANS-6-[2-SUBSTITUTEDPYRROL-1-YL)ALKYL]-4-HYDROXYPYRAN-2-ONES

[75] Inventor: Carl L. Heifetz, Ann Arbor, Mich.

[73] Assignee: Warner-Lambert Company, Morris Plains, N.J.

[21] Appl. No.: 64,972

[22] Filed: Jun. 18, 1987

[51] Int. Cl.$^4$ ...................... A61K 31/40; A61K 31/44
[52] U.S. Cl. .................................... 514/422; 514/423; 514/424; 514/427; 514/343
[58] Field of Search ............... 514/422, 423, 424, 427, 514/428, 343

[56] References Cited

U.S. PATENT DOCUMENTS 4,647,576  3/1987  Hoefle ................................. 514/422

OTHER PUBLICATIONS

S. Shadomy, et al., "Laboratory Studies with Antifungal Agents: Susceptibility Tests and Bioassays," pp. 991–999 in *Manual Clin. Microbiol.*, 4th Ed., Amer. Soc. for Microbiol., Washington, D.C., 1985.

Primary Examiner—Allen J. Robinson
Assistant Examiner—R. Kearse
Attorney, Agent, or Firm—Ronald A. Daignault

[57] ABSTRACT

A method of treating fungal infections comprises administering an antifungally effective amount of a trans-6-[2-(substitutedpyrrol-1-yl)alkyl]-4-hydroxypyran-2-one compound or a β,δ-hydroxyheptanoic acid corresponding thereto.

6 Claims, No Drawings

METHOD OF TREATING FUNGAL INFECTIONS WITH TRANS-6-[2-SUBSTITUTEDPYRROL-1-YL)AL-KYL]-4-HYDROXYPYRAN-2-ONES

BACKGROUND OF THE INVENTION

This invention relates to methods of treating fungal infections in mammals. More particularly, it is concerned with the use of certain trans-6-[2-(substituted-pyrrol-1-yl)alkyl]-4-hydroxy-pyran-2-one compounds in the treatment of fungal infections.

The past decade has been quite productive in the discovery of new antibacterial agents. Most of the new agents have been parenteral agents, with the improved activity primarily in the gram-negative component of the antibacterial spectrum.

However, there has not been corresponding development in the area of antifungal agents. The increasing efficacy and potency of antibacterial therapy seems to have created an ecologic niche that has been filled by superinfecting fungal pathogens. Yet, no new types of antifungal agents have appeared which offer promise in the treatment of the important systemic mycoses which occur in immunosuppressed hosts.

A number of potent antimicrobial compounds are available for the treatment of acute disease, but therapy for chronic infections is often frustrating. The development of antibacterial compounds that could be safely administered via the oral route for a long period (as in an outpatient setting) might make a major difference in the management of these chronic infections. Oral medications active against staphylococci, gram-negative rods, and fungi would make it possible for patients to be discharged earlier, or even to be managed without hospitalization.

SUMMARY OF THE INVENTION

It has been found, in accordance with the present invention, that certain trans-6-[2-(substitutedpyrrol-1-yl)alkyl]-4-hydroxypyran-2-one and the corresponding lactone ring-opened β,δ-dihydroxyheptanoic acid compounds are effective antifungal agents, useful in the treatment of fungal infection in mammals. The present invention provides a method of treating fungal infections in mammals comprising the administration of an antifungally effective amount of a compound having Formula I

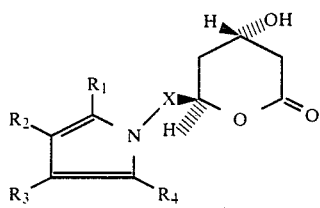

or aβ,δ-dihydroxyheptanoic acid compound of Formula II

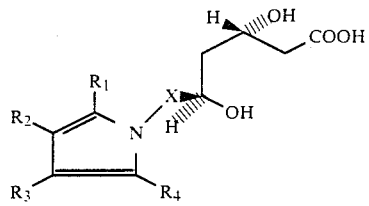

wherein X is $-CH_2-$, $-CH_2CH_2-$, or $-CH(CH_3)CH_2-$, in combination with a pharmaceutically acceptable carrier. In the compounds of Formula I or II, the substituent $R_1$ is selected from 1-naphthyl; 2-naphthyl; cyclohexyl; norbornenyl; 2-, 3-, or 4-pyridinyl; phenyl; or phenyl substituted with fluorine, chlorine, hydroxy, alkyl of from one to four carbon atoms, alkoxy of from one to four carbon atoms, or alkanoyloxy of from two to eight carbon atoms.

The substituents $R_2$ and $R_3$ are independently selected from hydrogen; chlorine; bromine; cyano; trifluoromethyl; phenyl; alkyl of from one to four carbon atoms; carboalkoxy of from two to eight carbon atoms; or $-CH_2OR_5$ where $R_5$ is hydrogen or alkanoyl of from one to six carbon atoms.

The group $R_4$ is alkyl of from one to four carbon atoms, cyclopropyl, cyclobutyl, or trifluoromethyl.

Also contemplated as falling within the scope of the method of this invention, is the use of pharmaceutically acceptable salts of the dihydroxy-acid compounds of Formula II.

As used throughout this specification and the appended claims, the term "alkyl" denotes a methyl group or a branched or unbranched saturated hydrocarbon group derived by the removal of a single hydrogen atom from an alkane.

The term "alkoxy" denotes an alkyl group, as previously defined, attached to the parent molecule through an oxygen atom.

The term "alkanoyloxy" means an alkyl group, as previously defined, attached to a carbonyl group and thence, through an oxygen atom, to the parent molecular residue.

The term "carboalkoxy" is meant to denote an alkyl group, as previously defined, attached to an oxygen atom and thence, through a carbonyl group to the parent molecular residue.

The term "norbornenyl" denotes a group derived by the removal of a single hydrogen atom (other than at a bridgehead carbon atom) from bicyclo[2.2.1]hept-2-ene.

DETAILED DESCRIPTION

The compounds useful in the method of this invention are described, together with a chemical process for their production, in U.S. Pat. No. 4,647,576 which is incorporated herein by reference.

The compounds are capable of existing either in the closed-ring lactone form of Formula I above, or may be converted to the corresponding β,δ-dihydroxyheptanoic acid open-ring form by the action of, for example, dilute aqueous base such as sodium hydroxide solution. The dihydroxyacid form may be employed as such in the method of this invention, or may be administered in the form of a pharmaceutically acceptable salt. The salts are formed by opening the lactone ring with the appropriate base such as the hydroxide or carbonate of the desired metal. Suitable salts are the sodium, potassium, calcium, and magnesium salts.

Specific examples of compounds contemplated as falling within the scope of the present invention include the following (named in the lactone form):

trans-6-[2-[2-Cyclobutyl-5-(4-fluorophenyl)-1H-pyrrol-1-yl]ethyl]tetrahydro-4-hydroxy-2H-pyran-2-one.

trans-6-[2-[2-Cyclohexyl-5-(4-fluorophenyl)-1H-pyrrol-1-yl]ethyl]tetrahydro-4-hydroxy-pyran-2-one.

trans-Tetrahydro-4-hydroxy-6-[2-(2-methyl-5-phenyl-1H-pyrrol-1-yl)ethyl-2H-pyran-2-one.

trans-6-[2-[2-(4-Chlorophenyl)-5-methyl-1H-pyrrol-1-yl]ethyl]tetrahydro-4-hydroxy-2H-pyran-2-one.

trans-Tetrahydro-4-hydroxy-6-[2-[2-(4-methoxyphenyl)-5-methyl-1H-pyrrol-1-yl]ethyl]-2H-pyran-2-one.

trans-6-[2-[2-([1,1'-Biphenyl]-4-yl)-5-methyl-1H-pyrrol-1-yl)ethyl]tetrahydro-4-hydroxy-2H-pyran-2-one.

trans-Tetrahydro-4-hydroxy-6-[2-[2-methyl-5-[3-(trifluoromethyl)phenyl]-1H-pyrrol-1-yl]ethyl]-2H-pyran-2-one.

trans-6-[2-[2-(2,5-Dimethylphenyl)-5-(1-methylethyl)-1H-pyrrol-1-yl]ethyl]tetrahydro-4-hydroxy-2H-pyran-2-one.

trans-6-[2-[2-(2,6-Dimethoxyphenyl)-5-(1-methylethyl)-1H-pyrrol-1-yl]ethyl]tetrahydro-4-hydroxy-2H-pyran-2-one.

trans-Tetrahydro-4-hydroxy-6-[2-[2-methyl-5-(2-naphthalenyl)-1H-pyrrol-1-yl]ethyl]-2H-pyran-2one.

trans-6-[2-(2-(Cyclohexyl-5-trifluoromethyl-1H-pyrrol-1-yl)ethyl]tetrahydro-4-hydroxy-2H-pyran-2-one.

trans-6-[2-[2-(4-Fluorophenyl)-3,4-dimethyl-5-(1-methylethyl)-1H-pyrrol-1-yl]ethyl]tetrahydro-4-hydroxy-2H-pyran-2-one.

trans-2-(4-Fluorophenyl)-5-(1-methylethyl)-1-[2-(tetrahydro-4-hydroxy-6-oxo-2H-pyran-2-yl)-ethyl]-1H-pyrrole-3,5-dicarboxylic acid.

trans-6-[2-[3,4-Dichloro-2-(3-fluorophenyl)-5-(1-methylethyl)-1H-pyrrol-1-yl]ethyl]tetrahydro-4-hydroxy-2H-pyran-2-one.

trans-2-(4-Fluorophenyl)-5-(1-methylethyl)-1-[(tetrahydro)-4-hydroxy-6-oxo-2H-pyran-2-yl)-ethyl]-1H-pyrrole-3,4-dicarbonitrile.

trans-6-[2-[3,4-Diacetyl-2-(4-fluorophenyl)-5-(1-methylethyl)-1H-pyrrol-1-yl]ethyl]tetrahydro-4-hydroxy-2H-pyran-2-one.

trans-Diethyl 2-(4-Fluorophenyl)-1-[2-(tetrahydro)-4-hydroxy-6-oxo-2H-pyran-2-yl)ethyl]-5-(trifluoromethyl)-1H-pyrrole-3,4-dicarboxylate.

trans-Bis(1-methylethyl) 2-(4-fluorophenyl)-5-(1-methylethyl)-1-[2-(tetrahydro)-4-hydroxy-6-oxo-2H-pyran-2-yl)ethyl]-1H-pyrrole-3,4-dicarboxylate.

trans-6-[2-[3,4-Diethyl-2-(4-fluorophenyl)-5-(1-methylethyl)-1H-pyrrol-1-yl]ethyl]tetrahydro-4-hydroxy-2H-pyran-2-one.

trans-6-[2-[2-(4-Fluorophenyl)-3,4-bis-(hydroxymethyl)-5-(1-methylethyl)-1H-pyrrol-1-yl]ethyl]tetrahydro-4-hydroxy-2H-pyran-2-one.

trans-1-Methylethyl 4-Chloro-2-(4-fluoro-phenyl)-5-(1-methylethyl)-1-[2-(tetrahydro)-4-hydroxy-6-oxo-2H-pyran-2-yl)ethyl]-1H-pyrrole-3-carboxylate.

trans-1-Methylethyl 4-Chloro-5-(4-fluorophenyl)-2-(1-methylethyl)-1-[2-(tetrahydro)-4-hydroxy-6-oxo-2H-pyran-2-yl)ethyl]-1H-pyrrole-3-carboxylate.

trans-Ethyl 5-(4-Fluorophenyl)-1-[2-(tetra-hydro)-4-hydroxy-6-oxo-2H-pyran-2-yl)ethyl-3-(trifluoromethyl)-1H-pyrrole-3-carboxylate.

trans-Ethyl 5-(4-Fluorophenyl)-2-(1-methyl-ethyl)-4-phenyl-1-[2-(tetrahydro-4-hydroxy-6-oxo-2H-pyran-2yl)-ethyl]-1H-pyrrole-3-carboxylate.

trans-6-[2-[3-Chloro-5-(4-fluorophenyl)-2-(1-methylethyl)-4-phenyl-1H-pyrrol-1-yl]ethyl]-tetrahydro-4-hydroxy-2H-pyran-2-one.

trans-6-[2-[2-(4-Fluorophenyl)-5-(1-methyl-ethyl)-3,4-diphenyl-1H-pyrrol-1-yl]ethyl]tetra-hydro-4-hydroxy-2H-pyran-2-one.

The antimicrobial susceptibilities of eleven strains of Candida albicans, two strains of Candida tropicans, and one strain each of Torulopsis glabrata and Cryptococcus neoformans to several representative compounds of the present invention were tested. For comparison, the known antifungal agents amphotericin-B and ketoconazole were also tested. Minimal inhibitory concentrations (MIC's) for each compound were determined using the microbroth dilution technique described by S. Shadomy, et al, "Laboratory Studies with Antifungal Agents: Susceptibility Tests and Bioassays," pp. 991–999 in Manual Clin. Microbiol., 4th Ed., Amer. Soc. For Microbiol., Washington, D.C., 1985. The compounds tested are as follows and the results of the testing appear in the following Table.

Compound 1—3,4-Dibromo-2-(4-fluorophenyl)-$\beta,\delta$-dihydroxy-5-(1-methylethyl)-1H-pyrrole-1-heptanoic acid, monosodium salt.

Compound 2—trans-4-Bromo-5-(4-fluorophenyl)-1[2-(tetrahydro-4-hydroxy-6-oxo-2H-pyran-2-yl)-ethyl]-2-(trifluoromethyl)-1H-pyrrole-3-carboxylic acid, ethyl ester.

Compound 3—3,4-Dichloro-2-(4-fluorophenyl)-$\beta,\delta$-hydroxy-5-(1-methylethyl)-1H-pyrrole-1-heptanoic acid, monosodium salt.

In therapeutic use as antifungal agents, the compounds are administered to the patient, preferably by oral administration, at dosage levels of from 40 mg to 600 mg per day. For a normal human adult of approximately 70 kg body weight, this translates into a dosage of about 0.5 mg/kg to about 8.0 mg/kg of body weight per day. The dosages may, however, be varied depending upon the condition and prior medical history of the patient, the severity of the condition being treated, and the activity of the compound employed in the pharmaceutical composition. Determination of the optimal dose in a particular case is within the skill of the art.

The daily dose may be administered once daily to the subject, or may be divided and administered in several separate doses in a single twenty-four hour period, for convenience.

TABLE

| | Antifungal Activity | | | | |
|---|---|---|---|---|---|
| Microorganism | MIC ($\mu$g/ml) at 24 Hours for Compound | | | | |
| (Strain) | AMP-B* | Keto** | 1 | 2 | 3 |
| Candida albicans | | | | | |
| B4b | 4 | .25 | 16 | 16 | 32 |
| M752 | 8 | .25 | 32 | 32 | 64 |
| ATCC 10231 | 4 | >.5 | 16 | 16 | 32 |
| 1570 | 8 | .25 | 16 | 32 | 64 |
| 1571 | 2 | .125 | 32 | 64 | 64 |

TABLE-continued

| Microorganism (Strain) | Antifungal Activity MIC (μg/ml) at 24 Hours for Compound | | | | |
|---|---|---|---|---|---|
| | AMP-B* | Keto** | 1 | 2 | 3 |
| 1574 | 4 | .25 | 16 | 32 | 64 |
| 1575 | 8 | .5 | 32 | 32 | 64 |
| 1576 | 4 | >.5 | 15 | 32 | 64 |
| 1577 | 8 | .125 | 16 | 32 | 32 |
| 1578 | 8 | .25 | 16 | 32 | 64 |
| 1579 | 4 | .5 | 16 | 32 | 64 |
| *Candida tropicans* | | | | | |
| ATCC 13803 | 8 | .5 | 64 | 64 | 128 |
| 1573 | 4 | >.5 | 16 | 16 | 32 |
| *Torulopsis glabrata* | | | | | |
| 1581 | 8 | >.5 | 128 | 128 | 128 |
| *Cryptococcus neoformans* | | | | | |
| 1678 | 4 | >.5 | 128 | 64 | 128 |

*Amphotericin-B
**Ketoconazole

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents. It can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppository preparations, a low-melting wax such as a mixture of fatty-acid glycerides and cocoa butter is melted, and the active ingredient is dispersed homogeneously therein, as by stirring. The moltent homogeneous mixture is then poured into conveniently sized molds and allowed to cool and solidify.

Powders and tablets preferably contain about 5% to about 70% of the active ingredient. Examples of suitable solid carriers are magnesium stearate, magnesium carbonate, talc, sugar, lactose, pectin, dextrin, starch, tragacanth, methyl cellulose, sodium carboxymethyl cellulose, and the like.

The term "preparation" is intended to include the formulation of the active compound with encapsulating material as carrier providing a capsule in which the active component (with or without other carriers) is surrounded by carrier. Similarly, cachets are included.

Tablets, powders, cachets, and capsules can be used as solid dosage forms suitable for oral administration.

Liquid form preparations include solutions, emulsions, and suspensions. Liquid preparations can be formulated in aqueous solution or in aqueous/alcohol solution with such materials as polyethylene glycol. Such solutions are prepared by dissolving the active component in water or aqueous/alcohol solution and adding suitable colorants, flavoring agents, stabilizers, and thickening agents as desired. Aqueous suspensions for oral use can be made by dispersing the finely divided active compound in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into using doses containing appropriate quantities of the active component. The unit dosage form can be a packaged preparation, the package containing discrete quantities of preparation, for example packeted tablets, capsules, or powders in vials or ampoules. The unit dosage form can also be a capsule, cachet, or tablet itself or can be the appropriate number of any of these packaged forms.

I claim:

1. A method of treating fungal infections in a mammal comprising administering to a mammal in need of said treatment an antifungally effective amount of a compound selected from the group consisting of compounds of Formula I and the corresponding β,δ-dihydroxyheptanoic acids of Formula II

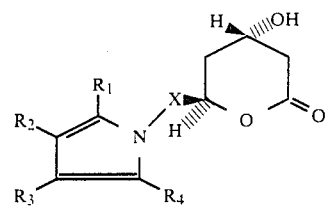

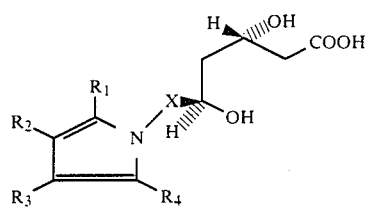

wherein
X is:
—CH$_2$—;
—CH$_2$CH$_2$—; or
—CH(CH$_3$)CH$_2$—;
R$_1$ is:
1-naphthyl;
2-naphthyl;
cyclohexyl;
norbornenyl;
2-pyridinyl;
3-pyridinyl;
4-pyridinyl;
phenyl; or
phenyl substituted with
fluorine,
chlorine,
hydroxy,
alkyl of from one to four carbon atoms,
alkoxy of from one to four carbon atoms, or
alkanoyloxy of from two to eight carbon atoms;
R$_2$ and R$_3$ are independently
hydrogen;
chlorine;
bromine;
cyano;
trifluoromethyl;
phenyl;
alkyl of from one to four carbon atoms;
carboalkoxy of from two to eight carbon atoms; or
—CH$_2$OR$_5$ wherein R$_5$ is hydrogen or alkanoyl of from two to six carbon atoms;
R$_4$ is alkyl of from one to four carbon atoms;

cyclopropyl;

cyclobutyl; or trifluoromethyl; or a pharmaceutically acceptable salt thereof, in combination with a pharmaceutically acceptable carrier.

2. The method of claim 1 wherein said administration is oral.

3. The method of claim 1 wherein said compound is a dihydroxyheptanoic acid compound of Formula II

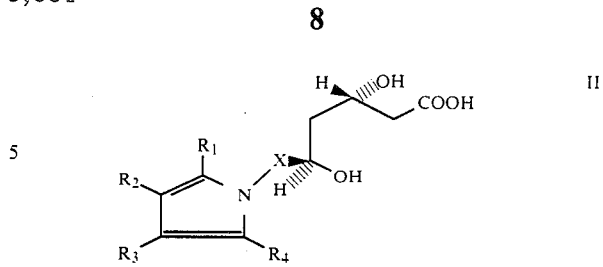

wherein $R_1$, $R_2$, $R_3$, $R_4$ are as defined above, or a pharmaceutically acceptable salt thereof, in combination with a pharmaceutically acceptable carrier.

4. The method of claim 1 wherein said compound is 3,4-dibromo-2-(4-fluorophenyl)-$\beta,\delta$-dihydroxy-5-(1-methylethyl)-1H-pyrrole-1-heptanoic acid, monosodium salt.

5. The method of claim 1 wherein said compound is trans-4-bromo-5-(4-fluorophenyl)-1-[2-(tetrahydro-4-hydroxy-6-oxo-2H-pyran-2-yl)-ethyl]-2-(trifluoromethyl)-1H-pyrrole-3-carboxylic acid, ethyl ester.

6. The method of claim 1 wherein said compound is 3,4-dichloro-2-(4-fluorophenyl)-$\beta,\delta$-hydroxy-5-(1-methylethyl)-1H-pyrrole-1-heptanoic acid, monosodium salt.

* * * * *